United States Patent [19]

Omura et al.

[11] 4,218,478
[45] Aug. 19, 1980

[54] TRICHOSTATIN AS AN ANTIPROTOZOAL AGENT

[76] Inventors: Satoshi Omura, 5-12-7 Seta, Setagaya-ku, Tokyo; Ruiko Oiwa, 384 Hazawacho, Kanagawa-ku, Yokohama, both of Japan

[21] Appl. No.: 1,246

[22] Filed: Jan. 5, 1979

[51] Int. Cl.² .................. A61K 31/165; A61K 31/16
[52] U.S. Cl. ................................... 424/324; 424/320
[58] Field of Search ............................... 424/320, 324

[56] References Cited
PUBLICATIONS

Tsuji et al., J. of Antibiotics, XXIX, No. 1, Jan. 1976, pp. 1–6.

*Primary Examiner*—Jerome D. Goldberg
*Attorney, Agent, or Firm*—Hesna J. Pfeiffer; James A. Arno; Julian S. Levitt

[57] ABSTRACT

Trichostatin (I) is disclosed to be useful as an antiprotozoal agent for the treatment of diseases in man and animals. Also disclosed are pharmaceutical compositions comprising trichostatin for treating protozoal infections. Trichostatin has the structure:

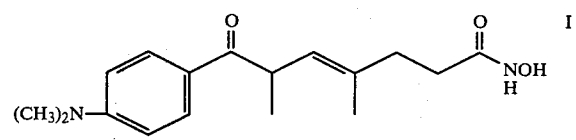

3 Claims, No Drawings

TRICHOSTATIN AS AN ANTIPROTOZOAL AGENT

BACKGROUND OF THE INVENTION

This invention relates to the use of trichostatin (I) as an antiprotozoal agent.

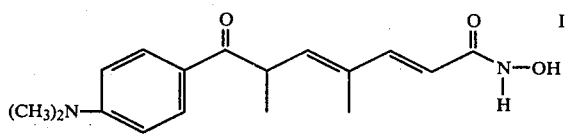

This invention also relates to pharmaceutical compositions comprising trichostatin which are useful in treating protozoal infections in man and animals.

Trichostatin is a known compound (*J. Antibiotics*, 29, No. 1, Jan. 1976) and is reported to be useful as an antifungal agent. Unexpectedly it has been discovered that trichostatin is also useful in combating infections in man and animals caused by protozoa. Specifically, it has been discovered that trichostatin is unexpectedly active against the following protozoal scourges of human and animal health:

*Trichomonas vaginalis* (the causitive organism of human trichomoniasis);

*Trichomonas foetus* (the causitive organism of bovine abortion);

*Histamonas meleagridis* (the causitive organism of histomoniasis);

*Entamoeba histolytica, Entamoeba erbi*, and the like (the causitive organisms of amoebiasis);

*Giardia lamblia* (the causitive organism of giardiasis); and

*Trypanosoma brucei* (one of the causitive organisms of African trypanasomiasis).

DETAILED DESCRIPTION OF THE INVENTION

The antiprotozoal effect of trichostatin is observed in both human and veterinary practices at a daily dosage level of from 1.0 mg to 1.0 g per kg of body weight. The optimum range for treatment of all classes of protozoal infection is a daily dosage of from 25 to 250 mg per kg of body weight; such dosage is preferably divided into 3 or 4 aliquots for delivery throughout the day. The treatment cycle typically runs for a period of seven days or until the treated individual is asymptomatic; but, of course, it will be recognized, and left to the discretion of the therapist, that the length of treatment and the dosage to be administered depend to a large extent upon the age, general health and weight of the host; the preferred course of treatment also depends upon the method of delivery of trichostatin, on the frequency of administration, and on the severity of the individual's infection.

The preferred route of delivery of trichostatin for purposes of this invention is by oral administration—a particularly preferred form being tablets comprising 100 to 250 mg of trichostatin in addition to the conventional tablet matrix elements. An example of such a formulation is given below.

A delivery in the form of ointments, suppositories or sustained delivery devices, especially for vaginal infections, is also contemplated by this invention. When employing this form of delivery, trichostatin is uniformly distributed in a suitably chemotherapeutic vehicle. The concentration of trichostatin in such topical delivery systems is such that a unit dosage lies in the range indicated above. The vehicle is preferably a semi-liquid or semi-solid type and the final preparation may be in the form of a suppository, if desired. Oil and water types of emulsions or creams as well as aqueous jellies such as those prepared with any of a number of jelling agents such as acacia, tragacanth, bentonite, alginic acid and the like are suitable vehicles. The vehicle may also be a viscous aqueous gel containing one or more ingredients such as hydroxyethyl cellulose and sodium carboxymethyl cellulose, jelling agents such as pectin, gum tragacanth, sodium aliginate and other vegetable jelling agents. It should be mentioned that a useful guide in determining dosage range, which is frequently expressed in terms of mg/kg body weight, is made available by the method described in Cuckler, et al., "Chemotherapeutic and Tolerance Studies on Amino-nitrothiazoles" *Antibiotics and Chemotherapy*, Volume 5, No. 10 pp. 540–550, (1955). The following U.S. Patents are incorporated herein by reference since they individually and collectively describe the state of the art as it regards topical formulations and sustained delivery systems:

| U.S. Pat. | 3,719,759 | (March 6, 1973) |
| U.S. Pat. | 3,133,863 | (May 19, 1964) |
| U.S. Pat. | 3,875,300 | (April 1, 1975) |
| U.S. Pat. | 3,639,566 | (February 1, 1972) |
| U.S. Pat. | 3,594,468 | (July 20, 1971) |
| U.S. Pat. | 3,991,760 | (November 16, 1976) |

A parenteral route of delivery by injection according to the above dosage range, is not preferred but might be utilized for generalized infections. In parenteral administration, the unit dosage comprises trichostatin (preferably in the form of a readily water soluble acid addition salt such as the hydrochloride, for example) in a sterile water solution; alternatively, the unit dose may be packaged in the form of a suitable powder intended for solution at the time of injection. Typical formulations are described below.

EXAMPLE 1

Preparation of Pharmaceutical Compositions

One such unit dosage form is prepared by mixing 250 mg trichostatin with 20 mg of lactose and 5 mg of magnesium stearate and placing the mixture into a No. 3 gelatin capsule. Similarly, by employing more of the active ingredient and less lactose, other dosage forms can be put up in No. 3 gelatin capsules; should it be necessary to prepare larger dosages, larger capsules or compressed tablets can also be prepared. The following examples are illustrative of the preparation of pharmaceutical formulations:

| TABLET | PER TABLET |
|---|---|
| Trichostatin | 250 mg. |
| Cornstarch, U.S.P. | 6 mg. |
| Dicalcium Phosphate | 192 mg. |
| Lactose, U.S.P. | 190 mg. |
| Magnesium stearate | balance |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| TOPICAL OINTMENT | |
| --- | --- |
| Trichostatin | 250 mg. |
| Polyethylene Glycol 4000 U.S.P. | 400 mg. |
| Polyethylene Glycol 400 U.S.P. | 1.0 gram. |

What we claim is:

1. A method of treating human and animal diseases caused by protozoal infections comprising administering to humans or animals in need of anti-protozoal treatment an anti-protozoal therapeutically effective amount of a compound having the structural formula:

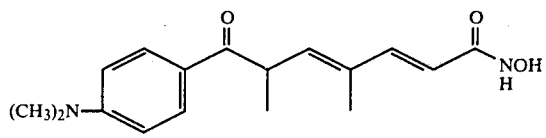

2. A method of treating trichomoniasis according to claim 1.

3. A method of treating amoebiasis according to claim 1.